US011643643B2

(12) United States Patent
Bode et al.

(10) Patent No.: US 11,643,643 B2
(45) Date of Patent: May 9, 2023

(54) ARTIFICIAL NON-RIBOSOMAL PEPTIDE SYNTHASES AND THEIR USE

(71) Applicant: Johann Wolfgang Goethe-Universität Frankfurt am Main, Frankfurt am Main (DE)

(72) Inventors: Helge B. Bode, Oberursel (DE); Kenan Bozhüyük, Frankfurt (DE); Florian Fleischhacker, Friedberg (DE)

(73) Assignee: Johann Wolfgang Goethe-Universität Frankfurt am Main, Frankfurt am Main (DE)

( * ) Notice: Subject to any disclaimer, the term of this patent is extended or adjusted under 35 U.S.C. 154(b) by 167 days.

(21) Appl. No.: 16/076,069

(22) PCT Filed: Feb. 8, 2017

(86) PCT No.: PCT/EP2017/052768
§ 371 (c)(1),
(2) Date: Aug. 7, 2018

(87) PCT Pub. No.: WO2017/137443
PCT Pub. Date: Aug. 17, 2017

(65) Prior Publication Data
US 2020/0181598 A1   Jun. 11, 2020

(30) Foreign Application Priority Data
Feb. 8, 2016   (DE) .......................... 102016001382.6

(51) Int. Cl.
C12N 9/88    (2006.01)
C12N 15/70   (2006.01)
C12P 21/00   (2006.01)

(52) U.S. Cl.
CPC .............. *C12N 9/88* (2013.01); *C12N 15/70* (2013.01); *C12P 21/00* (2013.01)

(58) Field of Classification Search
CPC ...................................................... C12N 9/88
See application file for complete search history.

(56) References Cited

U.S. PATENT DOCUMENTS

2010/0285563 A1* 11/2010 Marahiel ................. C12P 21/02
                                                              435/183

FOREIGN PATENT DOCUMENTS

| WO | 2000/052152 | 9/2000 |
| WO | 2001/030985 | 5/2001 |
| WO | 2007/014076 | 2/2007 |
| WO | 2017/020983 | 2/2017 |

OTHER PUBLICATIONS

Bozhüyük et al., "De novo design and engineering of non-ribosomal peptide synthetases", Nature Chemistry, Mar. 2018, vol. 10, pp. 275-281.*
Haynes et al., "Unraveling Terminal C-Domain-Mediated Condensation in Fungal Biosynthesis of Imidazoindolone Metabolites", Biochemistry, 2011, vol. 50, pp. 5668-5679.*
Bloudoff, K. & Schmeing, T.M., "Structural and functional aspects of the nonribosomal peptide synthetase condensation domain superfamily: discovery, dissection and diversity", BBA—Protein and Proteomics, 2017, vol. 1865, pp. 1587-1604.*
International Search Report and Written Opinion; International Patent Application No. PCT/EP2017052768; dated May 15, 2017 (18 pages).
M. Winn et al. "Recent advances in engineering nonribosomal peptide assembly lines", Natural Product Reports, vol. 33, pp. 317-347, Jan. 1, 2016.
Bode et al., "Determination of the Absolute Configuration of Peptide Natural Products by Using Stable Isotope Labeling and Mass Spectrometry", Chemistry—A European Journal, vol. 18, pp. 2342-2348, Feb. 20, 2012.
Giessen et al., "Ribosome-independent biosynthesis of biologically active peptides: Application of synthetic biology to generate structural diversity", Federation of European Biochemical Societies, vol. 586, pp. 2065-2075, Jan. 9, 2012.
Schimming et al., "Yeast Homologous Recombination Cloning Leading to the Novel Peptides Ambactin and Xenolindicin", Chembiochem: A European Journal of Chemical Biology, vol. 15, pp. 1290-1294, Jun. 16, 2014.
Sieber et al., "Molecular mechanisms underlying nonribosomal peptide synthesis: approaches to new antibiotics", Chemical Reviews, American Chemical Society, vol. 105, No. 2, pp. 715-738, Feb. 1, 2005.
Calcott et al., "Genetic manipulation of non-ribosomal peptide synthetasis to generate novel bioactive peptide products", Biotechnology Letters, vol. 36, No. 12, pp. 2407-2416, Sep. 12, 2014.
Kries, Hajo, "Biosynthetic engineering of nonribosomal peptide synthetasis", Journal of Peptide Science, vol. 22, No. 9, pp. 564-570, Sep. 9, 2016.

* cited by examiner

*Primary Examiner* — Suzanne M Noakes
(74) *Attorney, Agent, or Firm* — Hamre, Mueller & Larson, P.C.

(57) ABSTRACT

The present invention pertains to a novel architecture of non-ribosomal peptide synthases (NRPS). The invention provides artificial NRPS wherein the naturally occurring terminal condensation or thioesterase-domain is replaced by internal condensation or dual condensation/epimerization domains. Moreover, the present invention enables the portability of terminal condensation domains to unrelated NRPS in respect of peptide release of linear peptides. The replacement results in a product independent release of the synthesized product and therefore enables the rational design of NRPS. The invention provides the new NRPS, nucleic acids encoding them, methods for artificial NRPS generation, and methods for producing non-ribosomal peptides.

19 Claims, 4 Drawing Sheets
Specification includes a Sequence Listing.

ARTIFICIAL NON-RIBOSOMAL PEPTIDE SYNTHASES AND THEIR USE

FIELD OF THE INVENTION

The present invention pertains to non-ribosomal peptide synthases with internal condensation domains for peptide release of linear and cyclic non-ribosomally synthesized peptides. The invention provides artificial NRPS wherein the naturally occurring terminal condensation or thioesterase-domain is replaced by internal condensation or dual condensation/epimerization domains. Moreover, the present invention enables the portability of terminal condensation domains to unrelated NRPS in respect of peptide release of linear peptides. The replacement results in a product independent release of the synthesized product and therefore enables the rational design of NRPS. The invention provides the new NRPS, nucleic acids encoding them, methods for artificial NRPS generation, and methods for producing non-ribosomal peptides.

DESCRIPTION

Non-ribosomal peptide synthetases (NRPSs) and polyketide synthases (PKSs) are multifunctional enzyme complexes harboring a modular architecture (Marahiel 1997). Numerous natural products synthesized by these enzyme classes are of pharmaceutical and/or biotechnological interest because of its medicinally relevant properties including antimicrobial (e.g. teixobactin), antitumor (e.g. bleomycin), antifungal (fengycin) and immunosuppressant (cyclosporin) activity (Ling et al. 2015, Ishizuka et al. 1967, Loeffler et al. 1986, Emmel et al. 1989). Although the peptidic compounds produced by NRPSs exhibit a broad range of bioactivity and a great structural variety (e.g. non-proteinogenic amino acids, N-methylation, epimerization, heterocycles), a common mode of synthesis is shared, the so called "multiple-carrier thiotemplate mechanism".

Figure 1:
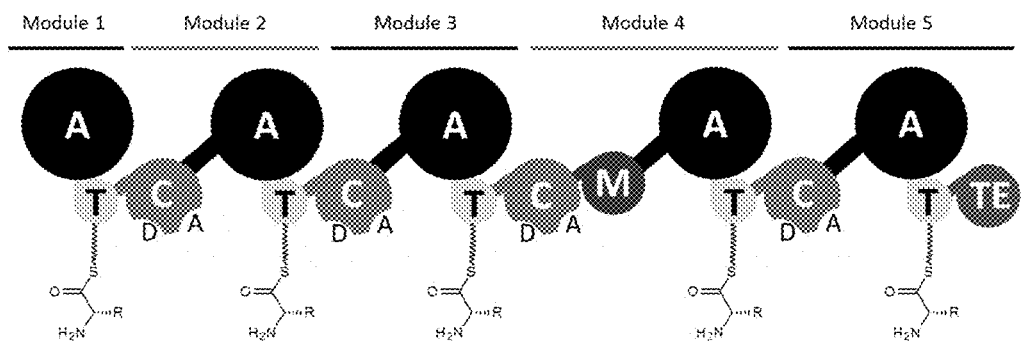

The structure of NRPSs is obligate modular (FIG. 1). A module is defined as the catalytic unit that incorporates one specific building block (e.g. amino acid) into the growing peptide chain (Marahiel 1997). NRPS modules can be subdivided into domains and each domain is responsible for a certain reaction step within peptide assembly. For example, a canonical elongation module is composed of three domains, denoted as core domains (FIG. 2):

- An adenylation (A) domain which selectively determines and activates substrates (usually amino-acids) as an amino acyl adenylate (FIG. 3).
- A peptidyl carrier protein (PCP), also called thiolation domain (T) binds the cofactor 4-phosphopantethein, to which the activated amino acid (AA) is covalently bound by thioester formation.
- A condensation (C) domain catalyzes peptide bond formation between the downstream and upstream located aminoacyl or peptidyl residues.

Figure 4:
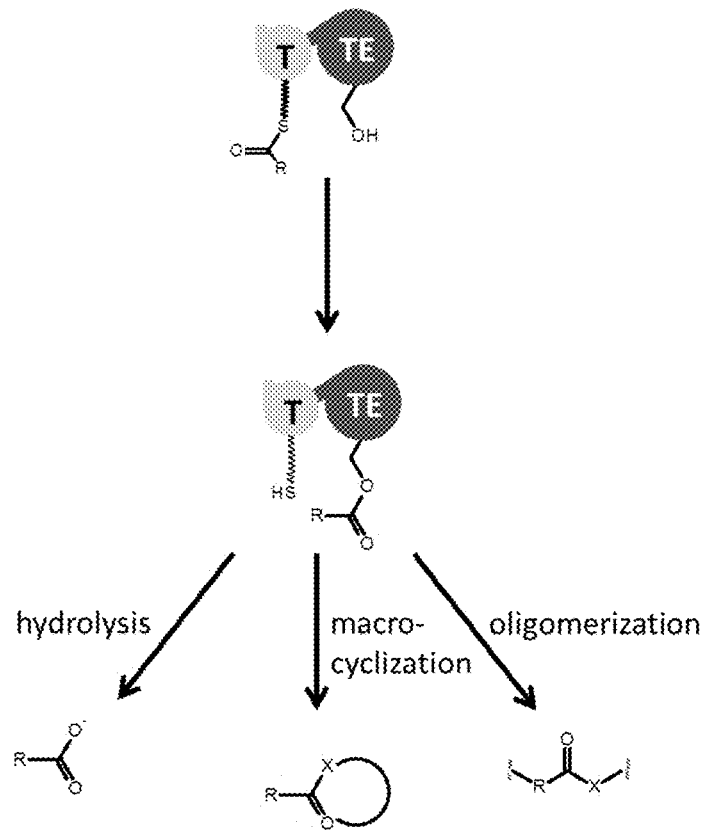

The first (N-terminal) module (start module) of a NRPS module often possesses no C domain and the last (C-terminal) module (termination module) usually contains a thioesterase (TE) domain (Marahiel et al. 1997). The TE domain usually is responsible for the release of linear (transfer to a water molecule), cyclic or branched cyclic peptides (amide or ester linkage) (FIG. 4).

The following domains may be included within a NRPS: C (condensation), Cy (heterocyclization), A (adenylation), T (thiolation) or PCP (peptidyl carrier protein), TE (thioesterase), E (epimerization), MT (methyltransferase), Ox (oxidase), and Re (reductase) domains. NRPSs generally have the following structure: A-T-(C-A-T)n-C-A-T-TE where A-T is the initiation module, C-A-T are the elongation modules, and C-A-T-TE is the termination module (FIG. 1). Within the individual modules, the following variations may, for example, occur: C is replaced by Cy, and E, MT, Ox, or Re are inserted; TE is replaced by C or Re. A complete assembly line may have an initiation module, a termination module, and somewhere between zero and n-2 elongation modules, where n is the number of monomers in the polymeric product. Exceptions to this rule may exist; e.g., the enterobactin synthetase, in which the TE domain acts as an oligomerase, so although it only has two modules, it hooks three of these dimeric products together to form a hexameric peptide product.

NRPSs are generally modular, and the series of catalytic steps moves from the amino to carboxy terminus of each polypeptide that makes up the NRPS. For example the NRPS that produces tyrocidine is made of three genes producing three polypeptides. TycA contains the initiation module; TycB contains three elongation modules, and TycC contains six additional elongation modules plus a termination module.

The following domains may be included within a PKS: KS (ketosynthase), AT (acyltransferase), T (thiolation), KR (ketoreductase), DH (dehydratase), ER (enoylreductase), TE (thioesterase). PKSs generally have the following structure: AT-T-(KS-AT-T)n-TE. AT-T is the initiation module, KS-AT-T are the elongation modules, and TE is the termination module. The structure of a PKS is very similar to NRPS structure. There are many examples (e.g., yersiniabactin, epothilone, bleomycin) of hybrid PKS-NRPS systems in which both types of assembly line are pieced together to form a coherent unit. Within each PKS module, one either finds a KR, a KR and DH, a KR and DH and ER, or no additional domains. These extra domains within a module determine the chemical functionality at the beta carbon (e.g., carbonyl, hydroxyl, olefin, or saturated carbon).

The power of NRPs and PKs as potential drugs lies in their diverse and complicated chemical structures. Generally, it is the intricacy of these natural products that makes them (or variants thereof) difficult to access synthetically. Several examples exist where laborious synthetic routes have been developed, rarely successfully, for NRPs or PKs. Additionally, various moieties on such molecules are inaccessible to modification by organic synthesis, or can only be produced at low yields using such techniques. This difficultly in synthesis and modification of the NRP and PK natural products underscores the need for alternative strategies to enhance synthesis and create variants of these molecules.

Despite the apparent modular structure of the NRPSs, it has, prior to our previous invention (EP15002340) and the present invention, in practice been difficult to swap domains so that the resulting NRPS is active. Substitution of one domain for another generally results in low yields (e.g., >10-fold reductions) and in the production of undesirable biosynthetic side products. These changes may be a result of disruptions of protein-protein interactions and due to the substrate specificities of C and TE domains, respectively. Thus, there is a need for new methods to produce novel NRPs and PKs and a need for methods that increase the yields of such NRPs and PKs.

For further general information on NRPSs and PKSs see Cane et al. (1998), Marahiel (1997), Sieber and Marahiel (2005) and Smith and Tsai (2007).

After activation and covalent binding of the first AA by the A-T didomain initiation module, peptide elongation proceeds by subsequent condensation with building blocks covalently tethered to T domains of the downstream (C terminal) elongation modules (C-A-T)n (Sieber and Marahiel 2005). All elongation reactions (peptide and amide bond formation) are mediated by ca 450 AA long C domains, located in between the upstream T and downstream A domain and are strictly unidirectional leading to a downstream-directed synthesis of the NRPS product (Samel et al. 2007). C domains catalyze the nucleophilic attack of the downstream T domain bound acceptor AA with its free α-amino group on the activated thioester of the upstream T domain bound donor AA or peptide.

Biochemical characterizations of C domains revealed insights into their catalytic role and substrate specificities. Via deletion experiments Stachelhaus and colleagues (1998) brought to light that C domains are indispensable for peptide bond formation. Furthermore, sequence alignments of several C domains revealed a highly conserved HHXXXDG (SEQ ID NO: 55) sequence motif (the so called "His motif") that is also present in acyltransferases (e.g. chloramphenicol acetyltransferase), NRPS E, and Cy domains (De Crecy-Lagard et al., 1995). Mutations of the second His residue in the conserved motif abolished activity in condensation assays (Sieber and Marahiel 2005).

Structures which include NRPS C domains have been determined by X-ray crystallography: a stand-alone C domain (Keating et al., 2002), a C-T didomain (Samel et al., 2007) and a C-A-T-TE termination module (Tanovic et al., 2008). C domains have a pseudo-dimer configuration, with both N- and C-terminal subdomains having cores with folds in the CoA dependent acyltransferase superfamily (Bloudoff et al. 2013). The active site is at the bottom of a "canyon" formed by the two subdomains, and is covered by a "latch" that crosses over from C to N subdomain. The catalytic center, including the HHXXXDG (SEQ ID NO: 55) (where X denotes any residue) motif, has two binding sites: one for the electrophilic donor substrate (the acyl group of the growing chain) and one for the nucleophilic acceptor substrate (the activated amino acid) (Rausch et al., 2007).

Although, little is known about the reaction C domains catalyze, biochemical characterization of different C domains from the tyrocidine synthetases (Belshaw et al. 1999; Clugston et al. 2003; Samel et al. 2007) revealed insights into their substrate specificities. All C domain characterizations were performed in vitro and used the same method to investigate the substrate acceptance of internal C domains. The upstream and/or downstream T domains were chemo-enzymatically primed (transfer of synthetic peptidyl-Ppan arms) with acceptor substrates by the use of the permissive PPTase Sfp (Belshaw et al. 1999; Samel et al. 2007). In summary, with this method it was shown that the acceptor site of the C domain exhibits a strong stereo and significant side chain selectivity (Rausch et al. 2007). The selectivity towards a specific side chain seems to be less pronounced at the donor site which exhibits strong stereoselectivity. C domains succeeding E domains show specificity towards the configuration of the C terminal residue bound at the donor site because the preceding E domain doesn't specifically catalyze the epimerization from L to D, yet provides a mixture of configurations. C domains immediately downstream of E domains were shown to be D-specific for the upstream donor and L-specific for the downstream acceptor, thus catalyzing the condensation reaction between a D- and an L-residue (Clugston et al., 2003).

C domains can be subdivided into functional and phylogenetic subtypes (Rausch et al. 2007). There are "standard" C domains within elongation modules like $^LC_L$ domains, which catalyze peptide bond formation between two L-AA, and $^DC_L$ domains connecting a L-amino acid to a growing peptide ending with a D-amino acid (Rausch et al., 2007). Starter C domains acylating the first amino acid with a carboxylic acid (often a β-hydroxyl fatty acid) and heterocyclization (CY) domains which catalyze both peptide bond formation and subsequent cyclization of cysteine, serine or threonine residues (Rausch et al. 2007). The homologous Epimerization (E) domain flips the chirality of the last amino acid in the growing peptide and Dual C/E domains catalyze both condensation and epimerization.

The most common way of multienzyme reactivation is via TE domains, which belong to the α/β-hydrolase superfamily (lipases, proteases and esterases) (Du and Lu 2009). These enzymes are ca. 280 amino acid long and are fused to most C-terminal T domain of the termination module (Sieber and Marahiel 2005; Kohli et al. 2001). In the last step of peptide assembly an active site serine of the TE domain carries out a nucleophilic attack on the T domainpeptidyl thioester to form a peptide-O-TE intermediate (Kohli et al. 2001). Deacylation of the intermediate involves either hydrolysis (attack of an exogenous nucleophile) to release a linear peptide or, in the case of cyclic products, reaction of an intramolecular nucleophile (N-, O-, or C-nucleophile). Hydrolytic release is observed for peptides such as vancomycin, whose peptide backbone is constrained by further post-synthetic oxidative cross-linking reactions.

Cyclizing TE domains provide a source of diversity and complexity as a variety of groups can be the nucleophile in the cyclization reaction: the N-terminal amino group (head-to-tail cyclization; e.g. tyrocidine A and gramicidin S), a side chain nucleophile (branched cyclic molecule; e.g. bacitracin A and daptomycin), and the β-hydroxyl group of a β-hydroxy fatty acid (e.g. surfactin) (Kohli et al., 2001).

Bruner et al. (2002) solved the first TE crystal structure of the surfactin biosynthesis cluster (SrfTE). In general NRPS TE domains are monomers and consist of an α/β-hydrolase fold with a catalytic triad ((Ser/Cys)-(His)-(Asp/Glu/Ser)) for substrate binding and catalysis via a covalently bound peptide-thioesterase intermediate. Furthermore, TE domains were found to exist in two distinct conformations, the open and the closed state. Differences between both states are restricted to a region of 40 amino acid residues covering most of the active site of the enzyme, which was named the lid region.

Unlike many other catalytic domains involved in the biosynthesis of non-ribosomal peptides, TE domains are highly diverse and consequently no model exists for predicting TE loading or release selectivity (Horsman et al. 2015). Phylogenetic analysis of TE sequences show that they do not cluster based on type of offloading chemistry they catalyze.

TE domains operate via a two-step mechanism, loading followed by release (Horsman et al. 2015). The active site Ser side chain alcohol is activated by the conserved His-Asp dyad, increasing its nucleophilicity. The T domain bound substrate approaches the activated Ser, mediated by the 4'Ppant cofactor. It has been hypothesized that the lid region opens to accommodate the presentation of thioester substrates. The deprotonated and conserved active site Ser attacks the substrate thioester and the resulting charged tetrahedral intermediate is stabilized in the oxyanion hole by hydrogen bonding from two backbone amide groups. This intermediate is resolved by loss of the 4'Ppant thiolate, generating the acyl-TE intermediate. The second step (offloading) involves release of the acyl group. This step begins with the approach of an intramolecular or intermolecular nucleophile. Townsend and colleagues (2010, 2014) suggested that the active-site histidinium ion is deprotonated by the departing thiolate and thus capable of activating the incoming nucleophile (Korman et al. 2010, Gaudelli and Townsend 2014). The nucleophile adds into the carbonyl of the acyl-TE intermediate and the tetrahedral intermediate is once again stabilized by the oxyanion hole. Finally the seryl alkoide is released with concerted protonation and the product leaves the active site.

Major insights into TE substrate specificity were gained by Trauger (2000) and Tseng (2002). By the use of synthetic SNAC-peptides (N-acetylcysteamin) they were able to show that TE domains are selective for the stereochemistry as well as the sidechain of the N-terminal AA residue. They also revealed that the AA next to the peptidyl-O-TE forming AA (C terminal AA) is important for peptide hydrolysis and cyclization, whereas all other AA within the produced peptide seem to be not crucial. Furthermore, Kohli et al. (2001) revealed that the excised TE domain from the tyrocidine NRPS accepts a broad spectrum of SNAC-peptides, varying in length and composition, as substrates for cyclization.

A noticeably distinct feature of most fungal NRPS is the replacement of the TE domain with a terminal C, R, or T domain (Haynes et al. 2011). In addition to NAD(P)H-dependent R domains, C domains can also be involved in peptide release (Kopp and Marahiel 2007). Whereas most bacterial NRPS use TE domains to perform the cyclization, fungal NRPS as well as some NRPS from bacteria including the genera *Photorhabdus* and *Xenorhabdus* use this complementary strategy (Gao et al. 2012; Reimer et al. 2013).

In macrocyclic fungal NRPSs such as cyclosporine A, aureobasidin A, apicidin and ferrichrome A, each corresponding NRPS catalyzes peptide release via terminal condensation (Cterm) domains (Gao et al. 2012). In the NRPS paradigm, C domains are canonically categorized to catalyze the formation of a peptide bond between the growing peptidyl-S-$T_n$ from module n and the activated aminoacyl-S-$T_{n+1}$ using an active site histidine as the general base. Therefore, it is surprising that the Cterm domain is able to perform the equivalent head-to-tail linkage of a TE domain. The reaction relies on a serine residue of the highly conserved HHxxxDxxS motif in the active site for nucleophilic catalysis and the nucleophile is an intra-molecular amino group, rather than the next AA (Kopp and Marahiel 2007). Gao et al. (2012) revealed that Cterm cyclization activity requires the presence of a T domain. Furthermore, via construction of recombinant T-Cterm didomains they were able to show that noncognate T domains do not interact with the downstream Cterm domain. Therefore, protein-protein interactions between the Cterm and the upstream T domain seem to be specific and might rely on T domain sequence elements that are unique for recognition by C domains. However, although terminal C domains are cited as controlling the cyclization of NRPS-based intermediates, there is as yet no experimental evidence to illustrate their proposed catalytic activity (Haynes et al. 2011).

Besides Cterm domains that catalyze peptide release by cyclization, there are Cterm domains that catalyze the formation of an amide-bond between the linear T-domain bound peptide and an amine from the environment (Reimer et al. 2013; Fuchs et al. 2012, Gao et al. 2012). One example is the non-ribosomal rhabdopeptide biosynthesis cluster from *Xenorhabdus nematophila*. Here, the Cterm domain might be involved in the condensation of a biogenic amine (e.g., phenylethylamine derived from phenylalanine decarboxylation) with the peptide intermediate during the release process (Reimer et al. 2013; Fuchs et al., 2012).

Since 1995, when Marahiel et al. (WO200052152) were able to show that it is possible to recombine NRPS through exchanging adenylation-thiolation didomains, NRPS research came into focus (Marahiel et al. 1995). During the last two decades, there have been a lot of attempts to reprogram NRPS. Based on the crystal structure of the phenylalanine activating domain PheA (PDB-ID: 1AMU) Stachelhaus et al. were able to elucidate the specificity conferring AAs in the catalytic center (Conti et al. 1997, Stachelhaus et al. 1999). With this specificity conferring code, denoted as Stachelhaus-code it is possible to predict and to change substrate specificities of a A domain in vitro, (Khurana et al. 2010, Rausch et al. 2005, Röttig et al. 2011, Kries et al. 2014). The most obvious disadvantage of this attempt is its inapplicability in vivo. One major reason for this drawback is that C and TE domains also have selectivities resulting in substrate incompatibilities (Belshaw et al. 1999; Trauger et al. 2000; Tseng et al. 2002).

A further attempt (WO200130985, Marahiel et al.) to vary known NRPS biosynthetic clusters is based on the exchange of single domains, didomains or whole modules and the knowledge of exactly defined borders (linkers) between individual domains. With this invention it was only possible to alter a few NRPSs successfully by introduction of additional modules or deleting them. However, it never was possible to produce totally artificial NRPSs from the artificial de novo combination of modules. This would result in new NRPS not present in nature that would also produce new peptides. The problem of such exchanges or combinations always was the uncertainty concerning the compatibility of modules and/or domains between each other. The shortcomings resulting from the lack of a solution to the problem mentioned above is illustrated by the fact that almost no artificial peptides have been designed by this approach.

Another attempt (WO2007014076, Walsh et al.) to vary known NRPS biosynthetic clusters is based on mutagenesis of so called "assembly lines" other word for synthases. Mutagenesis of genes of NRPS is not subject of the present invention although the present inventive methods can be combined with a mutagenesis that will alter the generated NRPS and cause altered peptide synthesis. This mutagenesis could be useful for increasing the diversification of NRPS libraries and the NRPS clone numbers in the library.

A recently introduced method is the concept of "Exchange Units" (EUs) (EP15002340). This method enables the design of artificial NRPSs de novo. However, this method also failed to introduce a valid concept for peptide release and is constrained by TE domain specificities.

Despite the modular organization of NRPSs and the recently introduced concept of EUs, prior to the invention it has been very difficult to create artificial and functional NRPSs that produce novel compounds, because up to date there was no method for the efficient release of peptides assembled by artificial NRPSs available.

In view of the state of the art it was therefore an object of the present invention to provide a new architecture for NRPS that allows for a rational design of small peptidic/ketidyl molecules. The invention seeks to provide these novel NRPS multi-domain complexes and methods for non-ribosomal peptide/ketide design.

The above problem is solved in a first aspect by an artificial non-ribosomal peptide synthase (NRPS), comprising as C-terminal end in N- to C-terminal direction an adenylation (A) domain, a thiolation (T) domain, and a termination module, wherein the termination module comprises any one of a a heterologous terminal condensation domain ($C_{term}$), an internal condensation (C) domain, an internal condensation and epimerization (C/E)-didomain, a cyclization (Cy) domain or an epimerization (E) domain.

For the present invention, the following definitions shall be used:

By "assembly" is meant a set of domains. A plurality of assembly comprises an NRPS. One or more polypeptides may comprise a module. Combinations of modules can catalyze a series of reactions to form larger molecules. In one example, a module may comprise a C (condensation) domain, an A (adenylation) domain, and a peptidyl carrier protein domain.

For more structural information on A domains, C domains, didomains, domain-domain interfaces and complete modules see Conti et al. (1997), Sundlov et al. (2013), Samel et al. (2007), Tanovic et al. (2008), Strieker and Marahiel (2010), Mitchell et al. (2012) and Tan et al. (2015).

By "initiation module" is meant a module which is capable of providing a monomer to a second module (e.g., an elongation or termination module). In the case of an NRPS, an initiation module comprises, for example, an A (adenylation) domain and a PCP (peptidyl carrier protein) or T (thiolation) domain. The initiation module may also contain an E (epimerization) domain. In the case of a PKS, the initiation module comprises an AT (acetyltransferase) domain and an acyl carrier protein (ACP) domain. Initiation modules are preferably at the amino terminus of a polypeptide of the first module of an assembly line, and each assembly line preferably contains one initiation module.

By "elongation module" is meant a module which adds a monomer to another monomer or to a polymer. An elongation module may comprise a C (condensation), Cy (heterocyclization), E, MT (methyltransferase), Ox (oxidase), or Re (reductase) domain; an A domain; or a T domain. An elongation domain may further comprise additional E, Re, DH (dehydration), MT, NMet (N-methylation), AMT (Aminotransferase), or Cy domains.

By "termination module" is meant a module that releases the molecule (e.g., an NRP, PK, or combination thereof) from the assembly line. The molecule may be released by, for example, hydrolysis or cyclization. Termination modules may comprise a TE (thioesterase), $C_{term}$, or Re domain. The termination module is preferably at the carboxy terminus of a polypeptide of an NRPS or PKS. The termination module may further comprise additional enzymatic activities (e.g., oligomerase activity).

By "domain" is meant a polypeptide sequence, or a fragment of a larger polypeptide sequence, with a single enzymatic activity. Thus, a single polypeptide may comprise multiple domains. Multiple domains may form modules. Examples of domains include C (condensation), Cy (heterocyclization), A (adenylation), T (thiolation), TE (thioesterase), E (epimerization), MT (methyltransferase), Ox (oxidase), Re (reductase), KS (ketosynthase), AT (acyltransferase), KR (ketoreductase), DH (dehydratase), and ER (enoylreductase).

By "nonribsomally synthesized peptide," "nonribosomal peptide," or "NRP" is meant any polypeptide not produced by a ribosome. NRPs may be linear, cyclized or branched and contain proteinogenic, natural or non-natural amino acids, or any combination thereof. NRPs include peptides produced by an assembly line.

By "polyketide" is meant a compound comprising multiple ketyl units.

By "non-ribosomal peptide synthetase" or "non-ribosomal peptide synthase" is meant a polypeptide or series of interacting polypetides that produce a nonribosomal peptide, thus that is able to katalyse peptide bond formation without the presence of ribosomal components.

By "polyketide synthase" (PKS) is meant a polypeptide or series of polypeptides that produce a polyketide. By "alter an amount" is meant to change the amount, by either increasing or decreasing. An increase or decrease may be by 3%, 5%, 8%, 10%, 15%, 20%, 30%, 40%, 50%, 60%, 70%, 80%, 90%, 100%, or more.

By "altering a structure" any change in a chemical (e.g., covalent or noncovalent) bond as compared to a reference structure is meant.

By "mutation" an alteration in the nucleic acid sequence such that the amino acid sequence encoded by the nucleic acid sequence has at least one amino acid alteration from a naturally occurring sequence is meant. The mutation may, without limitation, be an insertion, deletion, frameshift mutation, or a missense mutation. This term also describes a protein encoded by the mutant nucleic acid sequence.

By "variant" a polypeptide or polynucleotide with at least 10%, 20%, 30%, 40%, 50%, 60%, 70%, 80%, 90%, 95%, or 99% sequence identity to a reference sequence is meant. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-150 indicating a closely related sequence (Altschul et al., 1990).

Another embodiment of the invention pertains to the artificial NRPS, wherein the C-terminal end of the NRPS is non-natural occurring, preferably wherein the A-domain and/or T-domain of the C-terminal end of the NRPS are heterologous to the termination module, preferably when the termination module comprises a heterologous $C_{term}$-domain. Herein, non-naturally occurring shall refer to an NRPS with a module sequence that is not natural occurring, meaning that this NRPS module sequence is found in any organism, but is completely artificially and rational designed according to the design rules of the present invention. The term "heterologous" when used to compare to modules of an NRPS with each other is meant to refer to two or more modules which are not found together within the same NRPS in nature. Therefore, "heterologous" modules are non-natural combination of NRPS modules i.e. combinations where at least two of the combined sequences are foreign with respect to each other.

One preferred embodiment of the invention pertains to the artificial NRPS, wherein the termination module does not comprise a thioesterase (TE)-domain.

In general, natural or artificial biosynthetic NRPS templates terminate with a termination module, composed of a C, A, T and TE domain. To apply the invention the last (C terminal) domain (TE, Re or $C_{term}$) has to be replaced by a Dual C/E, $^LC_L$, $^DC_L$, $C_{term}$, Cy or E domain originated from NRPS elongation modules and termination modules, respectively. In every case the NRPS template (without a peptide releasing enzyme) has to end with the last (C terminal) AA of the T domain from the termination module. Due to the difference of AA composition of the linker regions (T-TE, T-C), they have to be replaced completely by the C domain associated T-C linker.

The artificial NRPS according to the invention may end C-terminally with the sequence: A-T-termination module. Alternatively, the NRPS of the invention may end C-terminally with the linker sequence between the last T and the TE domain, i.e. the TE domain is simply deleted. This embodiment may furthermore comprise an additional set of amino acid C-terminally from that linker sequence, however, without the presence of one of the above mentioned termination domains.

In one embodiment the artificial NRPS according to the invention may comprise an initiation module.

Another embodiment of the invention then pertains to an artificial NRPS comprising at least one elongation module. The elongation module may be selected from any elongation module known for NRPS structures. Preferred examples of elongation modules are described herein above.

The artificial NRPS of the invention may also comprise in N- to C-terminal direction: an initiation module; and/or one or more elongation module(s); and the termination module.

The artificial NRPS of the invention are preferred wherein the NRPS does not consist of the domain structure $A_{valine}$-T-C/E-$A_{leucine}$-T-C-$A_{threonine}$-T-C/E-$A_{valine}$-T-$C_{term}$. In this case, the indices of the A domains indicate their amino acid specificity.

The initiation module of the NRPS of the invention may comprise an A- and a T-domain, or a C-, A-, and T-domain, or a heterocylization (Cy)-, A-, and T-domain, or a C/E-, A-, and T-domain.

The elongation module of the NRPS of the invention may comprise a C-, A, and T-domain, wherein the C-domain alternatively is a Cy-domain or C/E-domain. Furthermore, the NRPS of the invention may have one or more of the following modification domains which are inserted: E(epimerization)-, MT(methyltransferase)-, Ox(oxidase)-, and Re(reductase)-domain.

The artificial NRPS according to the invention may comprise more than 2, 3, 4, or 5 elongation modules, preferably comprising 5 to 1000, or 5 to 500, or 5 to 100 or 5 to 50 elongation modules. The length of the NRPS and its domain sequence is selected in accordance to the peptide product to be produced. The person of skill in the art of NRPS is aware of the general domain activity in NRPS and is able to design according to the herein provided instructions a NRPS in order to produce any given peptide product.

In one embodiment of the invention the artificial NRPS is composed of exchange units (EU), wherein the EU comprises an A-domain followed by a T- and a C-domain. EU according to the invention are preferably separated by a linker comprising the consensus amino acid sequence WNATE.

The general architecture of EU are described in the following:

A standard EU is defined as the composition of an A domain followed by a T and C domain. The first EU (start EU) sometimes possesses an additional C domain in front of the first NRPS A domain and the last (termination EU) is composed either of an A, T and TE domain or solely of a TE domain. In the latter case the EU next to the last EU is composed of an A and T domain. Additionally to the "standard domains" (C, A, T,) a Cy domain instead of a C domain and a $C_{term}$ domain in place of a TE domain can be present. Furthermore, modification domains like an E, MT domain or Ox domain can be included within the EUs.

Border region between two EU: The borders of standard EUs are defined by the consensus motive WNATE (amino acid code) within the C-A linkers. Linkers between NRPS domains previously were described by Marahiel et al. (WO2001130985). Every standard EU starts with the consensus motive WNATE, followed by A, T, C domains and stops with the AA in front of the N-terminal AA (W) of the next C-A linker consensus motive. A termination EU starts with the consensus motive WNATE, followed by an A, T and the terminal domain in accordance with the above descriptions of the invention. If the termination EU, used for the design of the assembly line just consists of a C domain (preferably internal) of any kind, the EU (A-T) next to this preferably ends with the last AA of the T domain.

Fusion of EUs: EUs, no matter of origin (bacteria, fungi, plants), can be designed and used as building blocks according to the definition of EUs like a molecular construction kit, if the following rule according the concatenation of EUs as well as the rule for the termination module of the present invention is met. To prevent any problems concerning incompatibilities between EUs the substrate specificities of the C domain must be strictly adhered to. This means that the specificity of the A domain of the downstream EU always has to fit the substrate specificities of the upstream C domain. The assembly of EUs can be achieved by methods of molecular biology, like Gibson Cloning, Yeast based TAR-cloning et cetera.

Artificial NRPS are preferred in context of the invention, which means that in some embodiments the NRPS comprises at least two NRPS domains from different species.

The artificial NRPS according to the invention may further comprise one or more polyketide synthase (PKS) domains.

Another aspect of the invention then pertains to a nucleic acid construct, comprising a nucleic acid sequence encoding for a NRPS as described herein before. NRPS domain sequences from various species are available in public databases. The term "encoding" with respect to the present invention shall have a meaning being in agreement with the general understanding in the pertinent art. A nucleic acid encodes a protein or NRPS of the invention of the nucleic acid sequence if in one open reading frame the nucleic acid sequence according to the genetic code codes for an amino acid sequence of the protein or NRPS of the invention.

Yet another embodiment of the invention also pertains to a library of nucleic acid constructs as described herein before, wherein each nucleic acid construct in the library encodes one or more adjoining domains of a domain sequence of an NRPS of the invention that is intended to be designed following the herein described design rules. The library of the invention in a preferred embodiment provides a totality of nucleic acid constructs which encodes a complete artificial NRPS of the invention. Therefore, the library ideally includes nucleic acid constructs that encode for an adenylation (A) domain, a thiolation (T) domain, and one or more nucleic acid which encodes a termination module, wherein the termination module comprises any one of a heterologous terminal condensation domain (Cterm), an internal condensation (C) domain, an internal condensation and epimerization (C/E)-didomain, a cyclization (Cy) domain or an epimerization (E) domain. Preferably the library comprises in addition nucleic acids encoding further NRPS domains of any kind as described herein before. In this way the library of the invention allows a user after design of an artificial NRPS of the invention to put the design into practice and to express the respective nucleic acids in a biological cell in order to obtain the designed NRPS protein and/or to directly produce the peptide of choice.

In one embodiment of the invention each nucleic acid construct of the library of the invention encodes for an EU as described before, or wherein at least one nucleic acid construct encodes for a termination module and one nucleic acid construct encodes for at least an A-followed by a T-domain, and, optionally, one or more further nucleic acid constructs encode for an EU as described before.

A further aspect of the invention then provides a biological cell comprising a nucleic acid construct as described before.

Therefore, the invention may also provide as one aspect a library of biological cells (strains), wherein each biological cell (strain) comprises a nucleic acid construct of the above described library.

The invention also provides a method for generating an NRPS. The method may comprise the expression of one or more nucleic acid encoding for the NRPS in a biological cell. The method may also comprising the use of the EU architecture described in the previous patent application.

Since the NRPS of the invention are useful for the generation of novel peptide compounds, there is furthermore provided a method for the production of a non-ribosomal peptide, comprising the use of an artificial NRPS of the invention.

The advantage of the design for NRPS of the invention is that no product specific terminal domains are necessary for a peptide release. Usually, the addition of peptide releasing enzymes, or the laborious selection of product specific terminal domains was necessary to produce a non-ribosomal peptide. Therefore, the method for the production of non-ribosomal peptides of the invention does not involve the use of a peptide release enzyme to release the peptide product from the NRPS.

The non-ribosomal peptide of the invention may be a linear or a cyclic peptide. When the peptide is cyclic peptide, the NRPS preferably comprises at least one C/E-domain, preferably as termination module. Non-ribosomal peptides produced according to the descriptions of the invention are preferably non-naturally occurring non-ribosomal peptides.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Schematic representation of a NRPS. The domains are colored: Adenylation (A, black), thiolation (T, light grey), condensation (C, grey), modification (M, dark grey), thioesterase (TE, dark grey). Donor (D) and acceptor (A) sites of the condensation domain.

Figure 2:
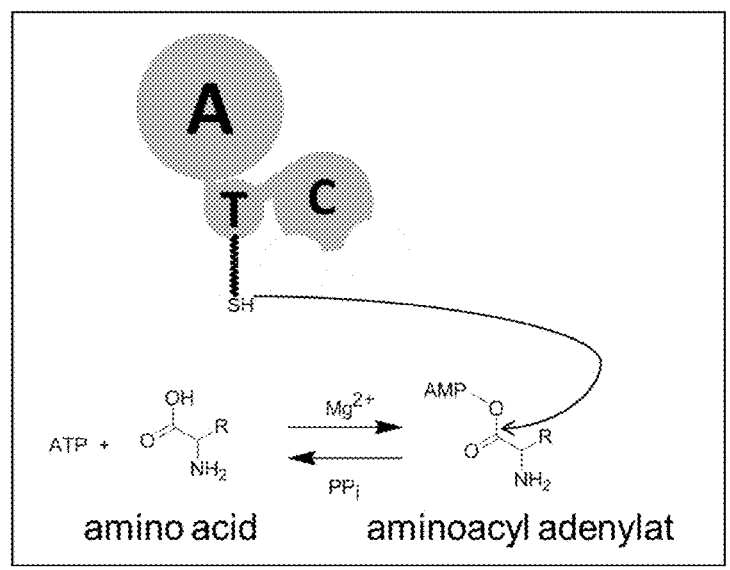

FIG. 2: Minimal NRPS (core domains). First, the A domain specifically recognizes a dedicated amino acid and catalyzes formation of the aminoacyl adenylate under consumption of ATP. Second, the activated aminoacyl adenylate is tethered to the free thiol group of the T domain bound phosphopantetheine (4'Ppan) cofactor. Third, the C-domain catalyzes peptide elongation.

Figure 3:
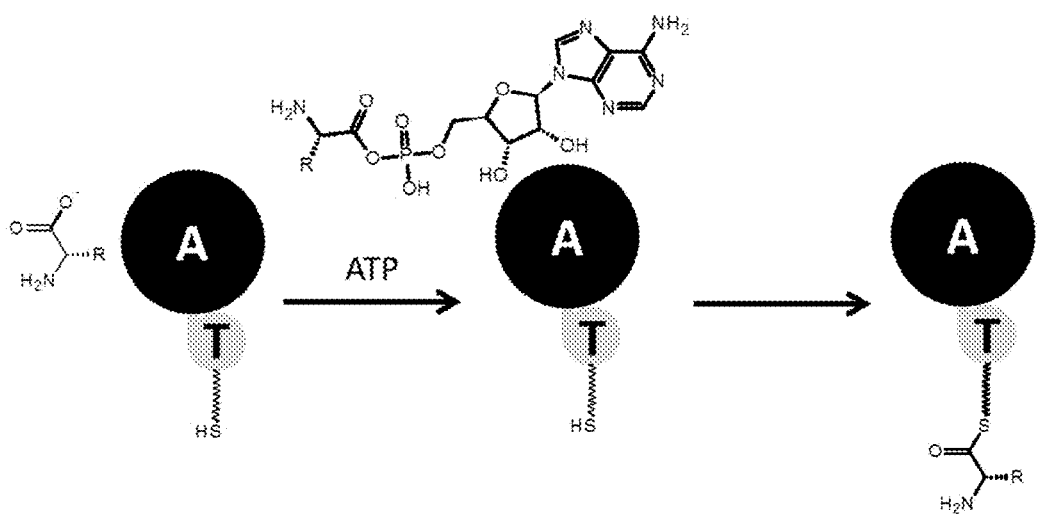

FIG. 3: Schematic diagram of NRPS adenylation and peptidyl carrier protein.

FIG. 4: Schematic diagram showing termination by the thioesterase domain (TE).

Figure 5:
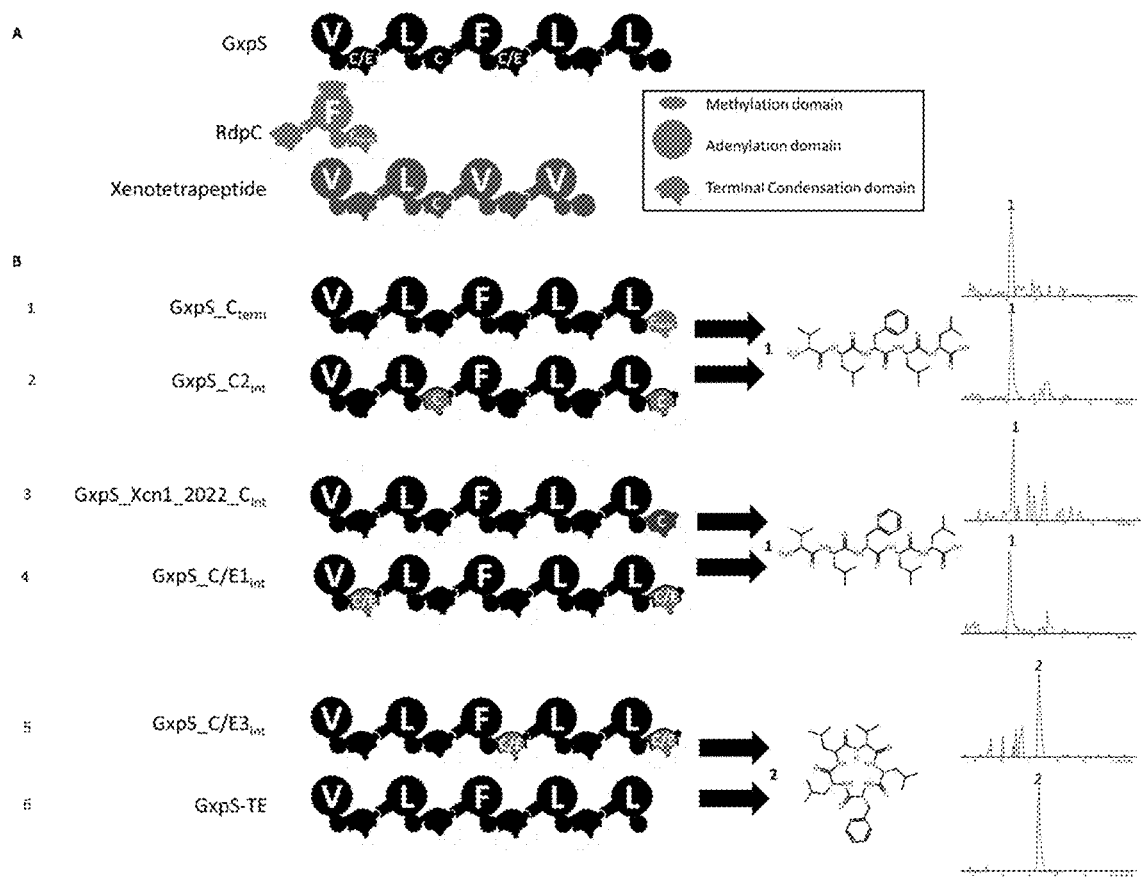

FIG. 5: A: Schematic representation of the NRPS involved in the experiments with GxpS and terminal C domains. B: Schematic representation of modified GxpS with a terminal C domain from RdpC (1), an internal C domain from GxpS (2) or Xenotetrapeptide NRPS (3), as well as an internal C/E domains from GxpS (4 and 5). GxpS without the TE is also shown (6). Additional extracted ion chromatograms show linear (1; m/z [M+H]$^+$=604.4) or cyclic (2; m/z [M+H]+=586.4) GameXPeptide.

Figure 6:
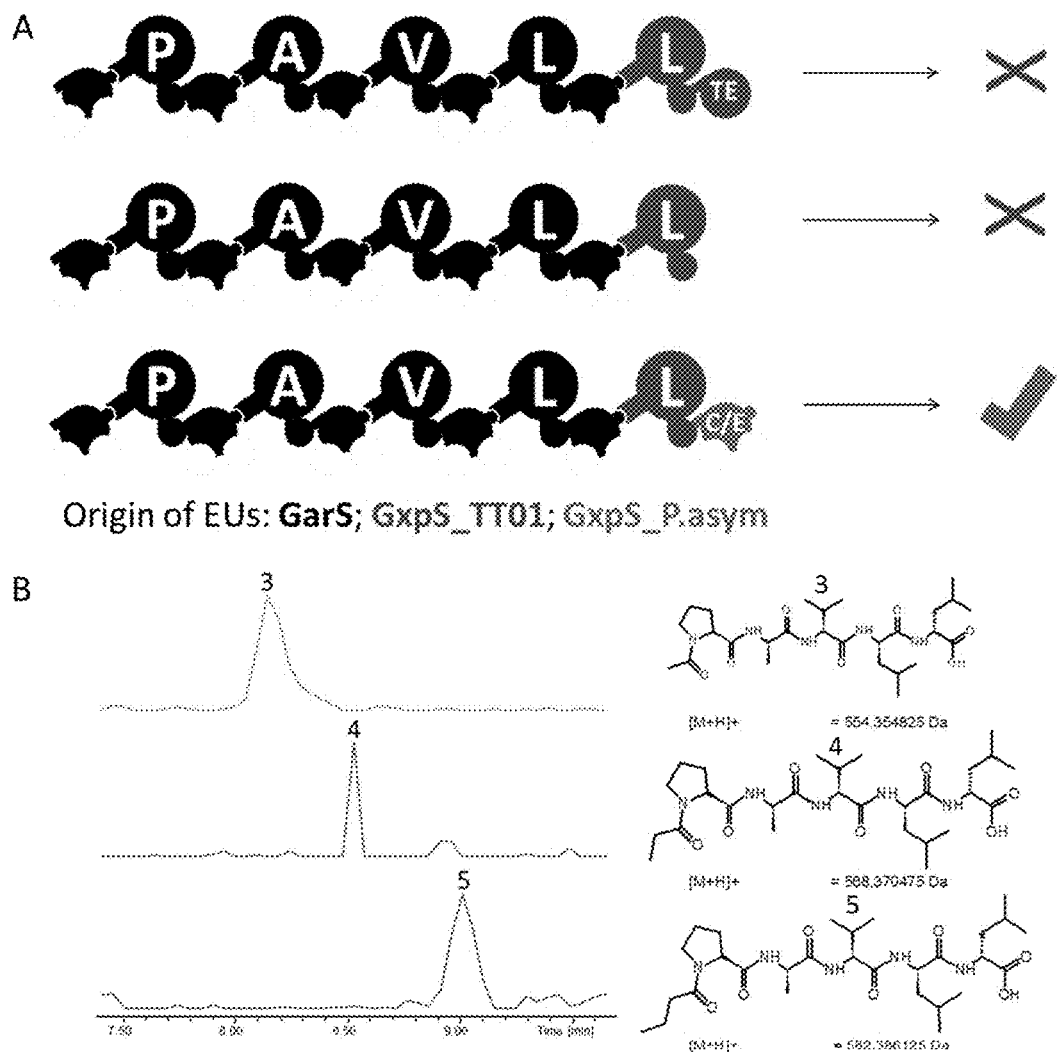

FIG. 6: A: Schematic representation of an artificial NRPSs with a TE (1), without a TE (2), and an internal Dual C/E domain from GxpS (3). The origin of EUs is indicated by their colour. B: Extracted ion chromatograms.

EXAMPLES

Materials and Methods

Cultivation of Strains:

All *E. coli*, *Photorhabdus* and *Xenorhabdus* strains were grown in liquid or solid LB-medium (pH 7.5, 10 g/L tryptone, 5 g/L yeast extract and 10 g/L NaCl). Solid media contained 1% (w/v) agar. *S. cerevisiae* strain CEN.PK 113-7D and derivatives were grown in liquid and solid YPD-medium (10 g/L yeast extract, 20 g/L peptone and 20 g/L glucose). Agar plates contained 2% (w/v) agar. Kanamycin (50 µg/ml) and G418 (200 µg/ml) were used as selection markers. All strains were cultivated at 30° C.

Molecular Biological Methods:

Genomic DNA of selected *Xenorhabdus* and *Photorhabdus* strains were isolated using the Qiagen Gentra Puregene Yeast/Bact Kit. Polymerase chain reaction (PCR) was performed with oligonucleotides obtained from Sigma-Aldrich and Eurofins Genomics (Table X3). Fragments with homology arms were amplified in a two-step PCR program using Phire Hot Start II DNA polymerase (Thermo Scientific) and for all other applications Phusion Hot Start II High-Fidelity DNA polymerase (Thermo Scientific) was used. Both polymerases were used according to the manufacturers' instructions. DNA purification was performed using MinE-lute PCR Purification Kit Qiagen). Plasmid isolation from *E. coli* was done by alkaline lysis.

Overlap Extension PCR-Yeast Homologous Recombination (ExRec):

Plasmids carrying the novel NRPS encoding gene(s) were constructed using ExRec cloning according to Schimming et al. (2014). Therefore, transformation of yeast cells was done according to the protocols from Gietz and Schiestl (2007). 100-2000 ng of each fragment was used for transformation. Successfully constructed plasmids were isolated from yeast transformants and retransformed in *E. coli* DH10B::mtaA by electroporation.

Expression of NRPS Templates:

For production of the biosynthetic NRPS templates 100 µl of an overnight culture in LB medium of *E. coli* DH10B::mtaA cells harboring the corresponding expression plasmids were used to inoculate 10 ml of LB medium containing 50 µg/mL kanamycin, 0.5 mg/ml L-arabinose, and 2% (v/v) XAD. The cells were grown at 37° C. up to 72 h.

Heterologous Expression and LC-MS Analysis:

Constructed plasmids were transformed into *E. coli* DH10B::mtaA. Strains were grown overnight in LB medium containing kanamycin. Overnight cultures were used for inoculation of 10 ml cultures containing kanamycin and 2% XAD-16. After incubation for 72 h at 30° C. the XAD-16 was harvested. One culture volume methanol was added and incubated for 30 min. The organic phase was filtrated and evaporated to dryness under reduced pressure. The extract was diluted in 900 µl methanol and a 1:10 dilution was used for LC-MS analysis as described previously (Fuchs et al.

2013; Fuchs et al. 2014). Confirmation of synthetic products was carried out using a gradient from 5-95% ACN (0.1% formic acid) over 14 min. All measurements were carried out by using an Ultimate 3000 LC system (Dionex) coupled to an Ama ZonX (Bruker) electron spray ionization mass spectrometer.

Experimental Examples:

In general NRPS exhibit a TE domain at the end of the assembly line. However, some have a terminal C ($C_{term}$) domain in place of a TE domain. $C_{term}$ domains release the synthesized peptides either by forming an amide-bond between the linear peptide and an amine from the environment or by cyclizing the peptide (Reimer et al. 2013, Fuchs et al. 2012, Gao et al. 2012). We constructed a recombinant GameXPeptide producing biosynthetic template (GxpS) (FIG. 5B-1) with a $C_{term}$ domain (GxpS_Cterm) from the rhabdopeptide producing biosynthetic cluster RdpA-C to determine the substrate range and applicability of its $C_{term}$ domain (RdpC) for NRPS regeneration. The recombinant NRPS GxpS_Cterm (FIG. 5B-1) is active but in contrast to our expectations the inventors observed a linear GameX-Peptide (1) without C-terminal amidation. Thus it was shown that $C_{term}$ domains can be used for the production of artificial linear peptides.

In further experiments with GxpS, internal C (GxpS_$C_{int}$) and Dual C/E (GxpS_C/$E_{int}$) domains were tested as TE domain alternatives (FIG. 5B). The inventors also deleted the GxpS TE domain without substitution (GxpS-TE). All recombinant NRPS were active. GxpS_$C_{int}$ produced linear (1), GxpS_C/$E_{int}$ linear (1) and/or cyclic (2) and GxpS-TE cyclic GameXPeptide (2). Thus the invention provides several ways of NRPS regeneration leading to the desired cyclic (or linear) peptide. A further improvement in comparison to naturally occurring TE domains seems to be the possibility of controlling cyclization or hydrolysis of the particular peptide.

Therefore, cloning artificial NRPS with a library of internal C domains at the end of the assembly line is much more constructive, cheaper and timesaving than assaying a whole set of TE domains in vitro without guarantee of success.

In the following, the inventors combined all gained insights like using the concept of EUs (EP application No. 1 500 234 0) and the applicability of internal C domains from elongation modules to create an artificial NRPS template capable of synthesizing a novel peptidic compound. For this purpose the building blocks from the gargantuanin synthase (GarS; unpublished data) and GxpS (FIG. 6a) were rebuilt. The artificial NRPS was designed in three variants to explore different peptide releasing strategies: (i) with a common TE domain from GxpS (FIG. 6A-1); (ii) without any peptide release catalyzing enzyme (NRPS ends with a T domain) (FIG. 6A-2); and (iii) with an internal C/E domain of module three from GxpS (FIG. 6A-3). According to our expectations, no product formation was observed for NRPS variants (i) and (ii). Yet, we observed the production of three novel linear lipo-penta-peptides with fatty acids varying in length (FIG. 6B).

In summary, the invention demonstrates how novel biosynthetic templates can be designed de novo, without any need of evolutionary optimized peptide releasing enzymes. Furthermore, it is confirmed that internal C and C/E domains easily can be recruited for the biotechnological production of novel peptides according to the invention, whereas naturally occurring TE domains are not applicable if the assembled peptide does not meet its substrate specificity range.

TABLE X1

Strains used and constructed in this work.

| Strain | Genotype | Reference |
|---|---|---|
| E. coli DH10B | F_mcrA (mrr-hsdRMS-mcrBC), 80lacZ □, M15, □ lacX74 recA1 endA1 araD 139 □ (ara, leu)7697 galU galK □ rpsL (Strr) nupG | Hanahan, 1983 |
| E. coli DH10B::mtaA | DH10B with mtaA from pCK_mtaA Δ entD | Schimming, 2014 |
| S. cerevisiae CEN. PK 113-7D | MATα, MAL2-8$^c$, SUC2 | Euroscarf |
| P. asymbiotica | | DSMZ |
| P. luminescens TT01 | | DSMZ |
| X. nematophila | | DSMZ |
| X. bovienii SS2004 | | DSMZ |
| E. coli DH10B::mtaA pFF1_GxpS_$C_{term}$ | E. coli DH10B::mtaA pFF1_GxpS_$C_{term}$, Kan$^R$ | this work |
| E. coli DH10B::mtaA pFF1_GxpS_C2$_{int}$ | E. coli DH10B::mtaA pFF1_GxpS_C2$_{int}$, Kan$^R$ | this work |
| E. coli DH10B::mtaA pFF1_GxpS_C/E1$_{int}$ | E. coli DH10B::mtaA pFF1_GxpS_C/E1$_{int}$, Kan$^R$ | this work |
| E. coli DH10B::mtaA pFF1_GxpS_C/E3$_{int}$ | E. coli DH10B::mtaA pFF1_GxpS_C/E3$_{int}$, Kan$^R$ | this work |
| E. coli DH10B::mtaA pFF1_GxpS_ohne_TE | E. coli DH10B::mtaA pFF1_GxpS_ohne_TE, Kan$^R$ | this work |
| E. coli DH10B::mtaA pFF1_GarS_GxpS_ohne_TE | E. coli DH10B::mtaA pFF1_GarS_GxpS_ohne_TE, Kan$^R$ | this work |
| E. coli DH10B::mtaA pFF1_GarS_GxpS_mit_TE | E. coli DH10B::mtaA pFF1_GarS_GxpS_mit_TE, Kan$^R$ | this work |
| E. coli DH10B::mtaA pFF1_GarS_GxpS_C/E3$_{int}$ | E. coli DH10B::mtaA pFF1_GarS_GxpS_C/E3$_{int}$, Kan$^R$ | this work |
| E. coli DH10B::mtaA pFF1_GxpS_Xcn1_C2$_{int}$ | E. coli DH10B::mtaA pFF1_GxpS_Xcn1_C2, Kan$^R$ | this work |

TABLE X2

Plasmids constructed in this work.

| Plasmid | Genotype | Reference |
|---|---|---|
| pFF1 | 2 μ ori, kanMX4, $P_{BAD}$ promoter, pCOLA ori, Kan$^R$, MCS | this work |
| pFF1_GxpS_$C_{term}$ | 2 μ ori, kanMX4, $P_{BAD}$ promoter, pCOLA ori, Kan$^R$, rdpC (from base 4597 to 5997) was inserted downstream of gxpS (from base 1 to 14625) | this work |
| pFF1_GxpS_C2$_{int}$ | 2 μ ori, kanMX4, $P_{BAD}$ promoter, pCOLA ori, Kan$^R$, gxpS from P. luminescens (from base 5177 to 6637 ) was inserted downstream of gxpS from P. asymbiotica (from base 1 to 14625) | this work |
| pFF1_GxpS_C/E1$_{int}$ | 2 μ ori, kanMX4, $P_{BAD}$ promoter, pCOLA ori, Kan$^R$, gxpS from P. asymbiotica (from base 1831 to 3336) | this work |

TABLE X2-continued

Plasmids constructed in this work.

| Plasmid | Genotype | Reference |
|---|---|---|
| pFF1_GxpS_C/E3$_{int}$ | was inserted downstream of gxpS from *P. asymbiotica* (from base 1 to 14625) 2 µ ori, kanMX4, P$_{BAD}$ promoter, pCOLA ori, Kan$^R$, rdpC from *P. asymbiotica* (from base 8200 to 9705) was inserted downstream of gxpS from *P. asymbiotica* (from base 1 to 14625) | this work |
| pFF1_GxpS_ohne_TE | 2 µ ori, kanMX4, P$_{BAD}$ promoter, pCOLA ori, Kan$^R$, gxpS from *P. asymbiotica* (from base 1 to 14784) | this work |
| pFF1_GarS_GxpS_ohne_TE | 2 µ ori, kanMX4, P$_{BAD}$ promoter, pCOLA ori, Kan$^R$, gxpS from *P. luminescens* TT01 (from base 13034 to 14944) was inserted downstream of garS (from base 1 to 14241) | this work |
| pFF1_GarS_GxpS_mit_TE | 2 µ ori, kanMX4, P$_{BAD}$ promoter, pCOLA ori, Kan$^R$, gxpS from *P. luminescens* TT01 (from base 13034 to 15699) was inserted downstream of garS (from base 1 to 14241) | this work |
| pFF1_GarS_GxpS_C/E3$_{int}$ | 2 µ ori, kanMX4, P$_{BAD}$ promoter, pCOLA ori, Kan$^R$, gxpS (nt) from *P. luminescens* (from base 13034 to 14785) followed by gxpS from *P. asymbiotica* (from base 8200 to 9705 ) was inserted downstream of garS (from base 1 to 14241) | this work |
| pFF1_GxpS_Xcn1_C2$_{int}$ | 2 µ ori, kanMX4, P$_{BAD}$ promoter, pCOLA ori, Kan$^R$, rdpC from *P. asymbiotica* (from base 5119 to 6567) was inserted downstream of gxpS from *P. asymbiotica* (from base 1 to 14625) | this work |

TABLE X3

Oligonucleotides used for primer construction in this work

| Plasmid | Oligonucleotide | Sequence (5'→3') | Template |
|---|---|---|---|
| pFF1_GxpS_C$_{term}$ | KB_Pau-P1 | TTATCGCAACTCTCTACT GTTTCTCCATACCCGTTT TTTTGGGCTAACAGGAG GAATTCCATGAAAGAGA GCATCGTGAG (SEQ ID Nr. 1) | *P. asymbiotica* |
| | KB_Pau-P2 | ATAATGCCACAGGCGAC CTG (SEQ ID Nr. 2) | |
| | KB_Pau-P3 | ATACGTCTGGCTCTACCG G (SEQ ID Nr. 3) | *P. asymbiotica* |
| | KB_Pau-P4 | GATTTCTGCTACCAGTTC AGCC (SEQ ID Nr. 4) | |
| | KB-Rdp3-FW | ATTTGCACATTGAATAAT CTGTTCCAATTCCCTGTG TTGGCTGAACTGGTAGC AGAAATCCGTAGCGCTC AAGACCATG (SEQ ID Nr. 5) | *X. nematophila* |
| | KB-Rdp3-RV | AAACAGTTCTTCACCTTT GCTCATGAACTCGCCAG AACCAGCAGCGGAGCCA GCGGATCCGTCATAAAA GTAACTGATATTTTC (SEQ ID Nr. 6) | |
| pFF1_GxpS_C2$_{int}$ | KB_Pau-P1 | TTATCGCAACTCTCTACT GTTTCTCCATACCCGTTT TTTTGGGCTAACAGGAG GAATTCCATGAAAGAGA GCATCGTGAG (SEQ ID Nr. 7) | *P. asymbiotica* |
| | KB_Pau-P2 | ATAATGCCACAGGCGAC CTG (SEQ ID Nr. 8) | |
| | KB_Pau-P3 | ATACGTCTGGCTCTACCG G (SEQ ID Nr. 9) | *P. asymbiotica* |
| | KB_Pau-P4 | GATTTCTGCTACCAGTTC AGCC (SEQ ID Nr. 10) | |
| | KB-PluC2-FW | ATTTGCACATTGAATAAT CTGTTCCAATTCCCTGTG TTGGCTGAACTGGTAGC AGAAATCTGCGCACAGA | *P. luminescens* TT01 |

TABLE X3-continued

Oligonucleotides used for primer construction in this work

| Plasmid | Oligonucleotide | Sequence (5'→3') | Template |
|---|---|---|---|
| | | TCTGTGCAC (SEQ ID Nr. 11) | |
| | KB-PluC2-RV | AAACAGTTCTTCACCTTT GCTCATGAACTCGCCAG AACCAGCAGCGGAGCCA GCGGATCCATGGACACA TACCTGAGTAGG (SEQ ID Nr. 12) | |
| pFF1_GxpS_C/E1$_{int}$ | KB_Pau-P1 | TTATCGCAACTCTCTACT GTTTCTCCATACCCGTTT TTTTGGGCTAACAGGAG GAATTCCATGAAAGAGA GCATCGTGAG (SEQ ID Nr. 13) | P. asymbiotica |
| | KB_Pau-P2 | ATAATGCCACAGGCGAC CTG (SEQ ID Nr. 14) | |
| | KB_Pau-P3 | ATACGTCTGGCTCTACCG G (SEQ ID Nr. 15) | P. asymbiotica |
| | KB_Pau-P4 | GATTTCTGCTACCAGTTC AGCC (SEQ ID Nr. 16) | |
| | KB-Pau-CE1-FW | ATTTGCACATTGAATAAT CTGTTCCAATTCCCTGTG TTGGCTGAACTGGTAGC AGAAATCGAGCACCATC AGTCTTTCG (SEQ ID Nr. 17) | P. asymbiotica |
| | KB-Pau-CE1-RV | AAACAGTTCTTCACCTTT GCTCATGAACTCGCCAG AACCAGCAGCGGAGCCA GCGGATCCATGGATACA CAACGAATCAGG (SEQ ID Nr. 18) | |
| pFF1_GxpS_C/E3$_{int}$ | KB_Pau-P1 | TTATCGCAACTCTCTACT GTTTCTCCATACCCGTTT TTTTGGGCTAACAGGAG GAATTCCATGAAAGAGA GCATCGTGAG (SEQ ID Nr. 19) | P. asymbiotica |
| | KB_Pau-P2 | ATAATGCCACAGGCGAC CTG (SEQ ID Nr. 20) | |
| | KB_Pau-P3 | ATACGTCTGGCTCTACCG G (SEQ ID Nr. 21) | P. asymbiotica |
| | KB_Pau-P4 | GATTTCTGCTACCAGTTC AGCC (SEQ ID Nr. 22) | |
| | KB-Pau-CE3-FW | ATTTGCACATTGAATAAT CTGTTCCAATTCCCTGTG TTGGCTGAACTGGTAGC AGAAATCGAGCAACATC GTGAAATCAG (SEQ ID Nr. 23) | P. asymbiotica |
| | KB-Pau-CE3-RV | AAACAGTTCTTCACCTTT GCTCATGAACTCGCCAG AACCAGCAGCGGAGCCA GCGGATCCATGAATGCA CAATTGGTCAG (SEQ ID Nr. 24) | |
| pFF1_GxpS_ohne_TE | KB_Pau-P1 | TTATCGCAACTCTCTACT GTTTCTCCATACCCGTTT TTTTGGGCTAACAGGAG GAATTCCATGAAAGAGA GCATCGTGAG( SEQ ID Nr. 25) | P. asymbiotica |
| | KB_Pau-P2 | ATAATGCCACAGGCGAC CTG (SEQ ID Nr. 26) | |
| | KB_Pau-P3 | ATACGTCTGGCTCTACCG G (SEQ ID Nr. 27) | P. asymbiotica |
| | KB-Pau-TE-RV | AAACAGTTCTTCACCTTT GCTCATGAACTCGCCAG AACCAGCAGCGGAGCCA GCGGATCCTAACGCATA AATCGGGTAATC (SEQ ID Nr. 28) | |

TABLE X3-continued

Oligonucleotides used for primer construction in this work

| Plasmid | Oligonucleotide | Sequence (5'→3') | Template |
|---|---|---|---|
| pFF1_GarS_GxpS_ohne_TE | LH 6 P1 | CGGATCCTACCTGACGCT TTTTATCGCAACTCTCTA CTGTTTCTCCATACCCGT TTTTTTGGGCTAACAGGA GGAATTCCATGCCTATGT CATGCAATCGTATC (SEQ ID Nr. 29) | X. bovienii SS2004 |
| | LH 6 P2 | GTTGCGCCAGTGCTAAC G (SEQ ID Nr. 30) | |
| | LH 6 P3 | CGTCTGGGTGTCAGTCCG (SEQ ID Nr. 31) | X. bovienii SS2004 |
| | LH 6 P4 | CTCTACCAGCAGTTGTTG TCGC (SEQ ID Nr. 32) | |
| | LH 6 P5 | CCCTGACCCGAGATCCG CAACAATTGATCCGGGA TGTATCCATCTTACCGCC GACAGAGCGACAACAAC TGCTGGTAGAGGGCAAT GGCCCGCAAACG (SEQ ID Nr. 33) | P. luminescens TT01 |
| | LH 6 P7 | AGAATCGGAACAACACC GGTAAACAGTTCTTCACC TTTGCTCATGAACTCGCC AGAACCAGCAGCGGAGC CAGCGGATCCTAGCGCA TAAATCGGGTAATCC (SEQ ID Nr. 34) | |
| pFF1_GarS_GxpS_mit_TE | LH 6 P1 | CGGATCCTACCTGACGCT TTTTATCGCAACTCTCTA CTGTTTCTCCATACCCGT TTTTTTGGGCTAACAGGA GGAATTCCATGCCTATGT CATGCAATCGTATC (SEQ ID Nr. 35) | X. bovienii SS2004 |
| | LH 6 P2 | GTTGCGCCAGTGCTAAC G(SEQ ID Nr. 36) | |
| | LH 6 P3 | CGTCTGGGTGTCAGTCCG (SEQ ID Nr. 37) | X. bovienii SS2004 |
| | LH 6 P4 | CTCTACCAGCAGTTGTTG TCGC (SEQ ID Nr. 38) | |
| | LH 6 P5 | CCCTGACCCGAGATCCG CAACAATTGATCCGGGA TGTATCCATCTTACCGCC GACAGAGCGACAACAAC TGCTGGTAGAGGGCAAT GGCCCGCAAACG (SEQ ID Nr. 39) | P. luminescens TT01 |
| | LH 6 P6 | AGAATCGGAACAACACC GGTAAACAGTTCTTCACC TTTGCTCATGAACTCGCC AGAACCAGCAGCGGAGC CAGCGGATCCCAGCGCC TCCGCTTCACAATTC (SEQ ID Nr. 40) | |
| pFF1_GarS_GxpS_C/E3$_{int}$ | LH 6 P1 | CGGATCCTACCTGACGCT TTTTATCGCAACTCTCTA CTGTTTCTCCATACCCGT TTTTTTGGGCTAACAGGA GGAATTCCATGCCTATGT CATGCAATCGTATC (SEQ ID Nr. 41) | X. bovienii SS2004 |
| | LH 6 P2 | GTTGCGCCAGTGCTAAC G (SEQ ID Nr. 42) | |
| | LH 6 P3 | CGTCTGGGTGTCAGTCCG (SEQ ID Nr. 43) | X. bovienii SS2004 |
| | LH 6 P4 | CTCTACCAGCAGTTGTTG TCGC (SEQ ID Nr. 44) | |
| | LH 6 P5 | CCCTGACCCGAGATCCG CAACAATTGATCCGGGA TGTATCCATCTTACCGCC GACAGAGCGACAACAAC TGCTGGTAGAGGGCAAT GGCCCGCAAACG (SEQ ID Nr. 45) | P. luminescens TT01 |

TABLE X3-continued

Oligonucleotides used for primer construction in this work

| Plasmid | Oligonucleotide | Sequence (5'→3') | Template |
|---|---|---|---|
| | LH 6 P8 | AACGGTAACATCGCCGGCGTCAGTACAACCGTATCCAGTGTAATGCTGTTGTCAGGCACCCTGATTTCACGATGTTGCTCGATCTCTGCCACCAGTTCCG (SEQ ID Nr. 46) | |
| | LH 3 P13 | GAGCAACATCGTGAAATCAG (SEQ ID Nr. 47) | P. asymbiotica |
| | LH 3 P14 | AGAATCGGAACAACACCGGTAAACAGTTCTTCACCTTTGCTCATGAACTCGCCAGAACCAGCAGCGGAGCCAGCGGATCCATGAATGCACAATTGGTCAG (SEQ ID Nr. 48) | |
| pFF1_GxpS_Xcn1_C2$_{int}$ | KB_Pau-P1 | TTATCGCAACTCTCTACTGTTTCTCCATACCCGTTTTTTTGGGCTAACAGGAGGAATTCCATGAAAGAGAGCATCGTGAG (SEQ ID Nr. 49) | P. asymbiotica |
| | KB_Pau-P2 | ATAATGCCACAGGCGACCTG (SEQ ID Nr. 50) | |
| | KB_Pau-P3 | ATACGTCTGGCTCTACCGG (SEQ ID Nr. 51) | P. asymbiotica |
| | KB_Pau-P4 | GATTTCTGCTACCAGTTCAGCC (SEQ ID Nr. 52) | |
| | KB_XcnC2_FW | ATTTGCACATTGAATAATCTGTTCCAATTCCCTGTGTTGGCTGAACTGGTAGCAGAAATCTGCGTACAACGTCATGCG (SEQ ID Nr. 53) | X. nematophila |
| | KB_XcnC2_RV | AAACAGTTCTTCACCTTTGCTCATGAACTCGCCAGAACCAGCAGCGGAGCCAGCGGATCCATGAATACATAACGATTCAGG (SEQ ID Nr. 54) | |

R. D. Gietz, R. H. Schiestl, *Nat Protoc.* 2007; 2(1), 35-7.

S. W. Fuchs, K. A. J. Bozhüyük, D. Kresovic, F. Grundmann, V. Dill, A. O. Brachmann, N. R. Waterfield, H. B. Bode, *Angew. Chem. Int. Ed.* 2013, 52, 4108-4112.

[40] S. W. Fuchs, F. Grundmann, M. Kurz, M. Kaiser, H. B. Bode, *Chembiochem* 2014, 15, 512-516.

O. Schimming, F. Fleischhacker, F. I. Nollmann, H. B. Bode, *Chembiochem* 2014, 15(9), 1290-4.

The invention claimed is:

1. An artificial non-ribosomal peptide synthase (NRPS), comprising as C-terminal end in N- to C-terminal direction an adenylation (A) domain, a thiolation (T) domain, and a termination module, wherein the termination module releases a synthesized molecule selected from a non-ribosomal peptide, polyketide, or combination thereof from the NRPS, wherein the termination module comprises any one of a heterologous terminal condensation domain ($C_{term}$), an internal condensation (C) domain, an internal condensation and epimerization (C/E)-didomain, a cyclization (Cy) domain or an epimerization (E) domain, wherein the termination module does not comprise a thioesterase (TE)-domain; and wherein in the NRPS, one or more of the following modification domains are inserted: E(epimerization)-, MT(methyltransferase)-, Ox(oxidase)-, and Re(reductase)-domain.

2. The artificial NRPS according to claim 1, wherein the C-terminal end of the NRPS is non-naturally occurring.

3. The artificial NRPS according to claim 1, comprising in N- to C-terminal direction an initiation module, and/or one or more elongation module(s), and the termination module.

4. The artificial NRPS according to claim 2, wherein the A-domain and/or T-domain of the C-terminal end of the NRPS are heterologous to the termination module.

5. The artificial NRPS according to claim 2, wherein the termination module comprises a heterologous $C_{term}$-domain.

6. The artificial NRPS according to claim 1, wherein the termination module comprises the C/E didomain.

7. A nucleic acid construct, comprising a nucleic acid sequence encoding for a NRPS according to claim 1.

8. A library of nucleic acid constructs, wherein each nucleic acid construct in the library encodes one or more adjoining domains of the NRPS according to claim 1, and wherein the totality of nucleic acid constructs in the library encodes the complete NRPS according to claim 1.

9. A biological cell comprising a nucleic acid construct according to claim 7.

10. A method for generating an NRPS according to claim 1, comprising assembling the A domain, the T domain, and the termination module of the NRPS.

11. A method for the production of a non-ribosomal peptide, the method comprising assembling the A domain, the T domain, and the terminal module of the NRPS according to claim 1.

12. A method for the production of a non-ribosomal peptide, the method comprising expressing the nucleic acid construct according to claim 7.

13. A method for the production of a non-ribosomal peptide, the method comprising expressing at least one of the nucleic acid constructs of the library according to claim 8.

14. A method for the production of a non-ribosomal peptide, the method comprising expressing the nucleic acid construct included in the biological cell according to claim 9.

15. An artificial non-ribosomal peptide synthase (NRPS), comprising as C-terminal end in N- to C-terminal direction an adenylation (A) domain, a thiolation (T) domain, and a termination module, wherein the termination module releases a synthesized molecule selected from a non-ribosomal peptide, polyketide, or combination thereof from the NRPS, wherein the termination module comprises an internal condensation (C) domain or an internal condensation and epimerization (C/E)-didomain, wherein the termination module does not comprise a thioesterase (TE)-domain.

16. The artificial NRPS according to claim 15, wherein the C-terminal end of the NRPS is non-naturally occurring.

17. The artificial NRPS according to claim 16, wherein the A-domain and/or T-domain of the C-terminal end of the NRPS are heterologous to the termination module.

18. The artificial NRPS according to claim 15, comprising in N- to C-terminal direction an initiation module, and/or one or more elongation module(s), and the termination module.

19. The artificial NRPS according to claim 15, wherein in the NRPS one or more of the following modification domains are inserted: E(epimerization)-, MT(methyltransferase)-, Ox(oxidase)-, and Re(reductase)-domain.

* * * * *

SEQUENCE LISTING

<160> NUMBER OF SEQ ID NOS: 55

<210> SEQ ID NO 1
<211> LENGTH: 80
<212> TYPE: DNA
<213> ORGANISM: P. asymbiotica

<400> SEQUENCE: 1
ttatcgcaac tctctactgt ttctccatac ccgtttttt gggctaacag gaggaattcc    60
atgaaagaga gcatcgtgag                                                80

<210> SEQ ID NO 2
<211> LENGTH: 20
<212> TYPE: DNA
<213> ORGANISM: P. asymbiotica

<400> SEQUENCE: 2
ataatgccac aggcgacctg                                                20

```
<210> SEQ ID NO 3
<211> LENGTH: 19
<212> TYPE: DNA
<213> ORGANISM: P. asymbiotica

<400> SEQUENCE: 3
atacgtctgg ctctaccgg                                              19

<210> SEQ ID NO 4
<211> LENGTH: 22
<212> TYPE: DNA
<213> ORGANISM: P. asymbiotica

<400> SEQUENCE: 4
gatttctgct accagttcag cc                                          22

<210> SEQ ID NO 5
<211> LENGTH: 79
<212> TYPE: DNA
<213> ORGANISM: X. nematophila

<400> SEQUENCE: 5
atttgcacat tgaataatct gttccaattc cctgtgttgg ctgaactggt agcagaaatc   60
cgtagcgctc aagaccatg                                              79

<210> SEQ ID NO 6
<211> LENGTH: 84
<212> TYPE: DNA
<213> ORGANISM: X. nematophila

<400> SEQUENCE: 6
aaacagttct tcacctttgc tcatgaactc gccagaacca gcagcggagc cagcggatcc   60
gtcataaaag taactgatat tttc                                        84

<210> SEQ ID NO 7
<211> LENGTH: 80
<212> TYPE: DNA
<213> ORGANISM: P. asymbiotica

<400> SEQUENCE: 7
ttatcgcaac tctctactgt ttctccatac ccgttttttt gggctaacag gaggaattcc   60
atgaaagaga gcatcgtgag                                             80

<210> SEQ ID NO 8
<211> LENGTH: 20
<212> TYPE: DNA
<213> ORGANISM: P. asymbiotica

<400> SEQUENCE: 8
ataatgccac aggcgacctg                                             20

<210> SEQ ID NO 9
<211> LENGTH: 19
<212> TYPE: DNA
<213> ORGANISM: P. asymbiotica

<400> SEQUENCE: 9
atacgtctgg ctctaccgg                                              19

<210> SEQ ID NO 10
<211> LENGTH: 22
```

```
<212> TYPE: DNA
<213> ORGANISM: P. asymbiotica

<400> SEQUENCE: 10
gatttctgct accagttcag cc                                              22

<210> SEQ ID NO 11
<211> LENGTH: 79
<212> TYPE: DNA
<213> ORGANISM: P. luminescens TT01

<400> SEQUENCE: 11
atttgcacat tgaataatct gttccaattc cctgtgttgg ctgaactggt agcagaaatc     60
tgcgcacaga tctgtgcac                                                  79

<210> SEQ ID NO 12
<211> LENGTH: 81
<212> TYPE: DNA
<213> ORGANISM: P. luminescens TT01

<400> SEQUENCE: 12
aaacagttct tcacctttgc tcatgaactc gccagaacca gcagcggagc cagcggatcc     60
atggacacat acctgagtag g                                               81

<210> SEQ ID NO 13
<211> LENGTH: 80
<212> TYPE: DNA
<213> ORGANISM: P. asymbiotica

<400> SEQUENCE: 13
ttatcgcaac tctctactgt ttctccatac ccgttttttt gggctaacag gaggaattcc     60
atgaaagaga gcatcgtgag                                                 80

<210> SEQ ID NO 14
<211> LENGTH: 20
<212> TYPE: DNA
<213> ORGANISM: P. asymbiotica

<400> SEQUENCE: 14
ataatgccac aggcgacctg                                                 20

<210> SEQ ID NO 15
<211> LENGTH: 19
<212> TYPE: DNA
<213> ORGANISM: P. asymbiotica

<400> SEQUENCE: 15
atacgtctgg ctctaccgg                                                  19

<210> SEQ ID NO 16
<211> LENGTH: 22
<212> TYPE: DNA
<213> ORGANISM: P. asymbiotica

<400> SEQUENCE: 16
gatttctgct accagttcag cc                                              22

<210> SEQ ID NO 17
<211> LENGTH: 79
<212> TYPE: DNA
<213> ORGANISM: P. asymbiotica
```

-continued

```
<400> SEQUENCE: 17
atttgcacat tgaataatct gttccaattc cctgtgttgg ctgaactggt agcagaaatc    60
gagcaccatc agtctttcg                                                79

<210> SEQ ID NO 18
<211> LENGTH: 81
<212> TYPE: DNA
<213> ORGANISM: P. asymbiotica

<400> SEQUENCE: 18
aaacagttct tcacctttgc tcatgaactc gccagaacca gcagcggagc cagcggatcc    60
atggatacac aacgaatcag g                                             81

<210> SEQ ID NO 19
<211> LENGTH: 80
<212> TYPE: DNA
<213> ORGANISM: P. asymbiotica

<400> SEQUENCE: 19
ttatcgcaac tctctactgt ttctccatac ccgttttttt gggctaacag gaggaattcc    60
atgaaagaga gcatcgtgag                                               80

<210> SEQ ID NO 20
<211> LENGTH: 20
<212> TYPE: DNA
<213> ORGANISM: P. asymbiotica

<400> SEQUENCE: 20
ataatgccac aggcgacctg                                               20

<210> SEQ ID NO 21
<211> LENGTH: 19
<212> TYPE: DNA
<213> ORGANISM: P. asymbiotica

<400> SEQUENCE: 21
atacgtctgg ctctaccgg                                                19

<210> SEQ ID NO 22
<211> LENGTH: 22
<212> TYPE: DNA
<213> ORGANISM: P. asymbiotica

<400> SEQUENCE: 22
gatttctgct accagttcag cc                                            22

<210> SEQ ID NO 23
<211> LENGTH: 80
<212> TYPE: DNA
<213> ORGANISM: P. asymbiotica

<400> SEQUENCE: 23
atttgcacat tgaataatct gttccaattc cctgtgttgg ctgaactggt agcagaaatc    60
gagcaacatc gtgaaatcag                                               80

<210> SEQ ID NO 24
<211> LENGTH: 80
<212> TYPE: DNA
<213> ORGANISM: P. asymbiotica

<400> SEQUENCE: 24
```

```
aaacagttct tcacctttgc tcatgaactc gccagaacca gcagcggagc cagcggatcc    60
atgaatgcac aattggtcag                                                80

<210> SEQ ID NO 25
<211> LENGTH: 80
<212> TYPE: DNA
<213> ORGANISM: P. asymbiotica

<400> SEQUENCE: 25
ttatcgcaac tctctactgt ttctccatac ccgttttttt gggctaacag gaggaattcc    60
atgaaagaga gcatcgtgag                                                80

<210> SEQ ID NO 26
<211> LENGTH: 20
<212> TYPE: DNA
<213> ORGANISM: P. asymbiotica

<400> SEQUENCE: 26
ataatgccac aggcgacctg                                                20

<210> SEQ ID NO 27
<211> LENGTH: 19
<212> TYPE: DNA
<213> ORGANISM: P. asymbiotica

<400> SEQUENCE: 27
atacgtctgg ctctaccgg                                                 19

<210> SEQ ID NO 28
<211> LENGTH: 81
<212> TYPE: DNA
<213> ORGANISM: P. asymbiotica

<400> SEQUENCE: 28
aaacagttct tcacctttgc tcatgaactc gccagaacca gcagcggagc cagcggatcc    60
taacgcataa atcgggtaat c                                              81

<210> SEQ ID NO 29
<211> LENGTH: 104
<212> TYPE: DNA
<213> ORGANISM: X. bovienii SS2004

<400> SEQUENCE: 29
cggatcctac ctgacgcttt ttatcgcaac tctctactgt ttctccatac ccgttttttt   60
gggctaacag gaggaattcc atgcctatgt catgcaatcg tatc                    104

<210> SEQ ID NO 30
<211> LENGTH: 18
<212> TYPE: DNA
<213> ORGANISM: X. bovienii SS2004

<400> SEQUENCE: 30
gttgcgccag tgctaacg                                                  18

<210> SEQ ID NO 31
<211> LENGTH: 18
<212> TYPE: DNA
<213> ORGANISM: X. bovienii SS2004

<400> SEQUENCE: 31
```

```
cgtctgggtg tcagtccg                                                    18

<210> SEQ ID NO 32
<211> LENGTH: 22
<212> TYPE: DNA
<213> ORGANISM: X. bovienii SS2004

<400> SEQUENCE: 32
ctctaccagc agttgttgtc gc                                               22

<210> SEQ ID NO 33
<211> LENGTH: 98
<212> TYPE: DNA
<213> ORGANISM: P. luminescens TT01

<400> SEQUENCE: 33
ccctgacccg agatccgcaa caattgatcc gggatgtatc catcttaccg ccgacagagc      60
gacaacaact gctggtagag ggcaatggcc cgcaaacg                              98

<210> SEQ ID NO 34
<211> LENGTH: 102
<212> TYPE: DNA
<213> ORGANISM: P. luminescens TT01

<400> SEQUENCE: 34
agaatcggaa caacaccggt aaacagttct tcacctttgc tcatgaactc gccagaacca      60
gcagcggagc cagcggatcc tagcgcataa atcgggtaat cc                         102

<210> SEQ ID NO 35
<211> LENGTH: 104
<212> TYPE: DNA
<213> ORGANISM: X. bovienii SS2004

<400> SEQUENCE: 35
cggatcctac ctgacgcttt ttatcgcaac tctctactgt ttctccatac ccgttttttt      60
gggctaacag gaggaattcc atgcctatgt catgcaatcg tatc                       104

<210> SEQ ID NO 36
<211> LENGTH: 18
<212> TYPE: DNA
<213> ORGANISM: X. bovienii SS2004

<400> SEQUENCE: 36
gttgcgccag tgctaacg                                                    18

<210> SEQ ID NO 37
<211> LENGTH: 18
<212> TYPE: DNA
<213> ORGANISM: X. bovienii SS2004

<400> SEQUENCE: 37
cgtctgggtg tcagtccg                                                    18

<210> SEQ ID NO 38
<211> LENGTH: 22
<212> TYPE: DNA
<213> ORGANISM: X. bovienii SS2004

<400> SEQUENCE: 38
ctctaccagc agttgttgtc gc                                               22
```

```
<210> SEQ ID NO 39
<211> LENGTH: 98
<212> TYPE: DNA
<213> ORGANISM: P. luminescens TT01

<400> SEQUENCE: 39
ccctgacccg agatccgcaa caattgatcc gggatgtatc catcttaccg ccgacagagc    60
gacaacaact gctggtagag ggcaatggcc cgcaaacg                            98

<210> SEQ ID NO 40
<211> LENGTH: 102
<212> TYPE: DNA
<213> ORGANISM: P. luminescens TT01

<400> SEQUENCE: 40
agaatcggaa caacaccggt aaacagttct tcacctttgc tcatgaactc gccagaacca    60
gcagcggagc cagcggatcc cagcgcctcc gcttcacaat tc                      102

<210> SEQ ID NO 41
<211> LENGTH: 104
<212> TYPE: DNA
<213> ORGANISM: X. bovienii SS2004

<400> SEQUENCE: 41
cggatcctac ctgacgcttt ttatcgcaac tctctactgt ttctccatac ccgttttttt    60
gggctaacag gaggaattcc atgcctatgt catgcaatcg tatc                    104

<210> SEQ ID NO 42
<211> LENGTH: 18
<212> TYPE: DNA
<213> ORGANISM: X. bovienii SS2004

<400> SEQUENCE: 42
gttgcgccag tgctaacg                                                  18

<210> SEQ ID NO 43
<211> LENGTH: 18
<212> TYPE: DNA
<213> ORGANISM: X. bovienii SS2004

<400> SEQUENCE: 43
cgtctgggtg tcagtccg                                                  18

<210> SEQ ID NO 44
<211> LENGTH: 22
<212> TYPE: DNA
<213> ORGANISM: X. bovienii SS2004

<400> SEQUENCE: 44
ctctaccagc agttgttgtc gc                                             22

<210> SEQ ID NO 45
<211> LENGTH: 98
<212> TYPE: DNA
<213> ORGANISM: P. luminescens TT01

<400> SEQUENCE: 45
ccctgacccg agatccgcaa caattgatcc gggatgtatc catcttaccg ccgacagagc    60
gacaacaact gctggtagag ggcaatggcc cgcaaacg                            98

<210> SEQ ID NO 46
```

```
<211> LENGTH: 100
<212> TYPE: DNA
<213> ORGANISM: P. luminescens TT01

<400> SEQUENCE: 46
aacggtaaca tcgccggcgt cagtacaacc gtatccagtg taatgctgtt gtcaggcacc    60
ctgatttcac gatgttgctc gatctctgcc accagttccg                         100

<210> SEQ ID NO 47
<211> LENGTH: 20
<212> TYPE: DNA
<213> ORGANISM: P. asymbiotica

<400> SEQUENCE: 47
gagcaacatc gtgaaatcag                                                20

<210> SEQ ID NO 48
<211> LENGTH: 100
<212> TYPE: DNA
<213> ORGANISM: P. asymbiotica

<400> SEQUENCE: 48
agaatcggaa caacaccggt aaacagttct tcacctttgc tcatgaactc gccagaacca    60
gcagcggagc cagcggatcc atgaatgcac aattggtcag                         100

<210> SEQ ID NO 49
<211> LENGTH: 80
<212> TYPE: DNA
<213> ORGANISM: P. asymbiotica

<400> SEQUENCE: 49
ttatcgcaac tctctactgt ttctccatac ccgttttttt gggctaacag gaggaattcc    60
atgaaagaga gcatcgtgag                                                80

<210> SEQ ID NO 50
<211> LENGTH: 20
<212> TYPE: DNA
<213> ORGANISM: P. asymbiotica

<400> SEQUENCE: 50
ataatgccac aggcgacctg                                                20

<210> SEQ ID NO 51
<211> LENGTH: 19
<212> TYPE: DNA
<213> ORGANISM: P. asymbiotica

<400> SEQUENCE: 51
atacgtctgg ctctaccgg                                                 19

<210> SEQ ID NO 52
<211> LENGTH: 22
<212> TYPE: DNA
<213> ORGANISM: P. asymbiotica

<400> SEQUENCE: 52
gatttctgct accagttcag cc                                             22

<210> SEQ ID NO 53
<211> LENGTH: 78
<212> TYPE: DNA
<213> ORGANISM: X. nematophila
```

-continued

```
<400> SEQUENCE: 53
atttgcacat tgaataatct gttccaattc cctgtgttgg ctgaactggt agcagaaatc      60
tgcgtacaac gtcatgcg                                                   78

<210> SEQ ID NO 54
<211> LENGTH: 81
<212> TYPE: DNA
<213> ORGANISM: X. nematophila

<400> SEQUENCE: 54
aaacagttct tcacctttgc tcatgaactc gccagaacca gcagcggagc cagcggatcc      60
atgaatacat aacgattcag g                                               81

<210> SEQ ID NO 55
<211> LENGTH: 7
<212> TYPE: PRT
<213> ORGANISM: Artificial
<220> FEATURE:
<223> OTHER INFORMATION: conserved His motif of C domains
<220> FEATURE:
<221> NAME/KEY: misc_feature
<222> LOCATION: (3)..(5)
<223> OTHER INFORMATION: X denotes any residue
<220> FEATURE:
<221> NAME/KEY: misc_feature
<222> LOCATION: (3)..(5)
<223> OTHER INFORMATION: Xaa denotes any residue

<400> SEQUENCE: 55

His His Xaa Xaa Xaa Asp Gly
1               5
```